United States Patent
Edmond

(10) Patent No.: US 8,361,116 B2
(45) Date of Patent: Jan. 29, 2013

(54) NON-PEDICLE BASED INTERSPINOUS SPACER

(75) Inventor: Elizabeth Watson Edmond, Ann Arbor, MI (US)

(73) Assignee: U.S. Spine, Inc., Salt Lake City, UT (US)

(*) Notice: Subject to any disclaimer, the term of this patent is extended or adjusted under 35 U.S.C. 154(b) by 647 days.

(21) Appl. No.: 11/690,884

(22) Filed: Mar. 26, 2007

(65) Prior Publication Data

US 2007/0225724 A1     Sep. 27, 2007

Related U.S. Application Data

(60) Provisional application No. 60/785,617, filed on Mar. 24, 2006.

(51) Int. Cl.
*A61B 17/70* (2006.01)

(52) U.S. Cl. ........................ 606/249; 606/248

(58) Field of Classification Search .............. 606/90, 606/248–253; 623/17.11–17.16
See application file for complete search history.

(56) References Cited

U.S. PATENT DOCUMENTS

| | | | |
|---|---|---|---|
| 5,496,318 A * | 3/1996 | Howland et al. | 606/249 |
| 5,885,284 A * | 3/1999 | Errico et al. | 606/252 |
| 6,126,660 A * | 10/2000 | Dietz | 606/90 |
| 6,440,169 B1 * | 8/2002 | Elberg et al. | 623/17.16 |
| 6,770,096 B2 * | 8/2004 | Bolger et al. | 623/17.16 |
| 6,949,123 B2 * | 9/2005 | Reiley | 623/17.11 |
| 7,238,204 B2 * | 7/2007 | Le Couedic et al. | 623/17.11 |
| 7,458,981 B2 * | 12/2008 | Fielding et al. | 606/279 |
| 7,476,251 B2 * | 1/2009 | Zucherman et al. | 623/17.15 |
| 7,520,887 B2 * | 4/2009 | Maxy et al. | 606/248 |
| 7,520,888 B2 * | 4/2009 | Trieu | 606/279 |
| 7,524,324 B2 * | 4/2009 | Winslow et al. | 606/248 |
| 7,585,313 B2 * | 9/2009 | Kwak et al. | 606/249 |
| 7,585,316 B2 * | 9/2009 | Trieu | 606/279 |
| 7,594,932 B2 * | 9/2009 | Aferzon et al. | 623/17.16 |
| 7,608,106 B2 * | 10/2009 | Reiley | 623/17.11 |
| 7,955,392 B2 * | 6/2011 | Dewey et al. | 623/17.16 |
| 8,075,593 B2 * | 12/2011 | Hess | 606/248 |
| 2005/0075643 A1 * | 4/2005 | Schwab et al. | 606/90 |
| 2005/0203512 A1 * | 9/2005 | Hawkins et al. | 606/61 |
| 2005/0261768 A1 * | 11/2005 | Trieu | 623/17.11 |
| 2006/0004447 A1 * | 1/2006 | Mastrorio et al. | 623/17.11 |
| 2006/0089654 A1 * | 4/2006 | Lins et al. | 606/90 |
| 2007/0100340 A1 * | 5/2007 | Lange et al. | 606/61 |
| 2007/0161992 A1 * | 7/2007 | Kwak et al. | 606/61 |
| 2008/0161818 A1 * | 7/2008 | Kloss et al. | 606/90 |
| 2008/0167655 A1 * | 7/2008 | Wang et al. | 606/90 |

* cited by examiner

*Primary Examiner* — Thomas Barrett
*Assistant Examiner* — Matthew Lawson
(74) *Attorney, Agent, or Firm* — Philips Ryther & Winchester; Matthew D. Thayne

(57) ABSTRACT

Spinal distraction apparatus includes at least one plate member having upper and lower surfaces adapted for placement between opposing upper and lower spinous processes having outer lateral surfaces. A pair of scissoring elements are hingedly affixed to the plate member to engage with the lateral surfaces of the spinous processes. A device is provided for locking the scissoring elements in position once a desired degree of contact is made. In a preferred configuration, the scissoring elements are sandwiched between a pair of opposing plate members, each having upper and lower surfaces adapted for placement between opposing upper and lower spinous processes, and the inner surfaces of the scissoring elements are concave. The device for locking the scissoring elements in position is a fastener that extends through a central portion of both scissoring elements and the plate members. The apparatus may further include a retractor with upper and lower plates for spreading the upper and lower spinous processes apart to receive the plate with scissoring element(s), and wherein the upper and lower surfaces of the plate member have notches to accommodate the upper and lower plates.

20 Claims, 2 Drawing Sheets

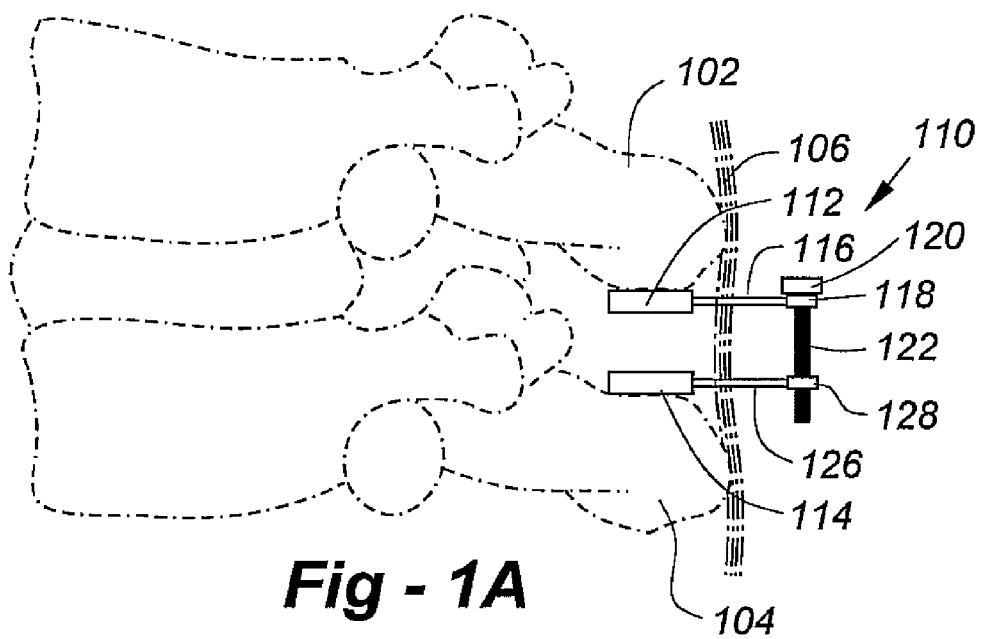
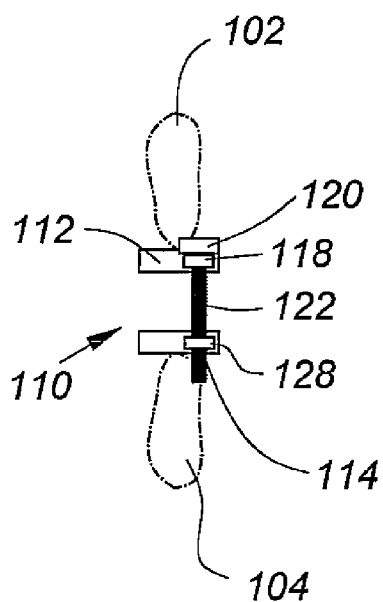
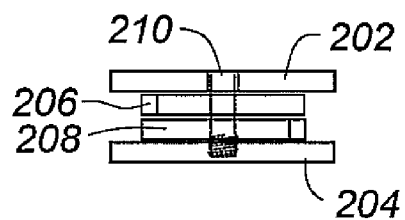
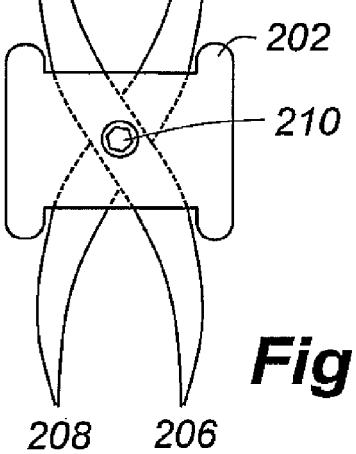
Fig - 1A
Fig - 1B
Fig - 2A
Fig - 2B

NON-PEDICLE BASED INTERSPINOUS SPACER

REFERENCE TO RELATED APPLICATION

This application claims priority from U.S. Provisional Patent Application Ser. No. 60/785,617, filed on Mar. 24, 2006, the entire content of which is incorporated herein by reference.

FIELD OF THE INVENTION

This invention relates generally to spinal stabilization devices and, in particular, to non-pedicle-based interspinous spacers.

BACKGROUND OF THE INVENTION

Natural intervertebral discs serve multiple purposes. First, they preserve correct anatomical spacing between adjacent vertebral bodies, allowing branching nerve bundles to function normally, without pain. Discs also facilitate natural flexion, extension, and lateral bending in support of daily physical activities. Discs further serve as "shock absorbers" for spinal loading.

However, for many reasons, natural discs can loose functionality, often leading to back pain. These sources may include physical trauma, degenerative disc disease, and other maladies. Today there are many options to stabilize spinal segments which may exhibit a loss of functionality. One option is spinal fusion, wherein a complete or partial discectomy is performed, with one or more cages or other mechanical devices being inserted into the disc space. Another option gaining in popularity is the use of "artificial discs," which typically include either a resilient central portion or mechanical elements that facilitate a certain degree of articulation.

Various types of intervertebral spacers are also available as valuable tools to promote spinal stabilization. Such devices may be used in conjunction with fusion, for example, to relieve pressure from the central vertebral column. Spacers may also be valuable in relieving spinal stenosis and other conditions resulting in back pain.

SUMMARY OF THE INVENTION

This invention resides in spinal distraction apparatus including at least one plate member having upper and lower surfaces adapted for placement between opposing upper and lower spinous processes having outer lateral surfaces. A pair of scissoring elements are hingedly affixed to the plate member. Each scissoring element has an end that extends beyond the upper surface of the plate member and an end that extends beyond the lower surface of the plate member, resulting in a pair of upwardly oriented scissoring elements with inner surfaces adapted for contact with the outer lateral surfaces of the upper spinous process and a pair of downwardly oriented scissoring elements with inner surfaces adapted for contact with the outer lateral surfaces of the lower spinous process. A device is provided for locking the scissoring elements in position once a desired degree of contact is made with the lateral surfaces.

In the preferred embodiment, the scissoring elements are sandwiched between a pair of opposing plate members, each having upper and lower surfaces adapted for placement between opposing upper and lower spinous processes, and the inner surfaces of the scissoring elements are concave. The device for locking the scissoring elements in position is a fastener that extends through a central portion of both scissoring elements and the plate members.

The apparatus may further include a retractor with upper and lower plates for spreading the upper and lower spinous processes apart to receive the plate with scissoring element(s), and wherein the upper and lower surfaces of the plate member have notches to accommodate the upper and lower plates.

BRIEF DESCRIPTION OF THE DRAWINGS

FIG. 1A is a lateral view of distraction apparatus according to the invention;

FIG. 1B is a posterior view of the distraction apparatus of FIG. 1A;

FIG. 2A is a drawing of a spinous process stabilization system according to the invention;

FIG. 2B is an end view of the system of FIG. 2A;

DETAILED DESCRIPTION OF THE PREFERRED EMBODIMENTS

Figure 3:
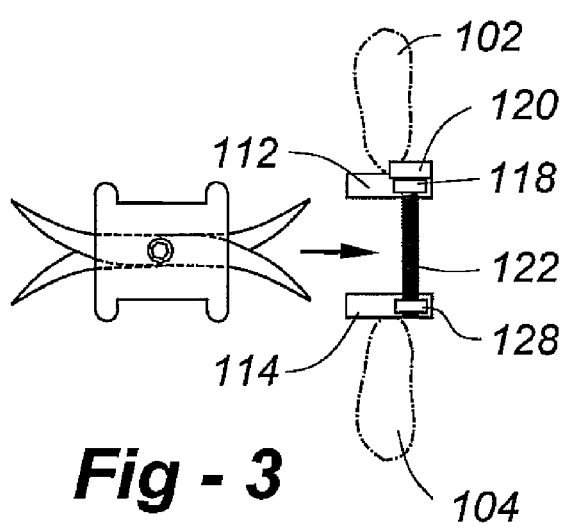
FIG. 3 is a drawing which shows a posterior view of spinous processes being distracted, and with the stabilization apparatus of FIGS. 2A and 2B being inserted.

Turning now to the drawings, FIG. 1A is a side view drawing which shows distraction apparatus according to the invention, indicated generally at 110. Such apparatus includes superior and inferior plates 112, 114, which are linked via members 116, 126 to elements 118, 128. Element 118 is a collar, which facilitates location, whereas element 128 is a threaded member which changes the relative position between plates 112, 114 in response to rotational force applied to head member 120. Rotation of head member 120 in one direction causes the distraction of spinous processes 102, 104, whereas rotation in the opposition direction allows the spinous processes to move toward one another. The supra spinous ligament is indicated at 106.

FIG. 1B is a posterior view of the system of FIG. 1A. The distraction mechanism proper, including collars 118, 128 and threaded element 122, are shown off to one side, though any appropriate placement facilitating distraction is acceptable. Indeed, distraction apparatus other than that just described are applicable to the invention, so long as the spacer described hereinbelow, may be accommodated.

Turning now to FIGS. 2A and 2B, these show a frontal view of an interspinous process spacer according to the invention, along with a side view (FIG. 2B). The spacer includes a plurality of opposing plates 202, 204, sandwiched therebetween are a pair of scissoring elements 206, 208. A threaded fastener used for tightening is indicated at 210.

Figure 4:
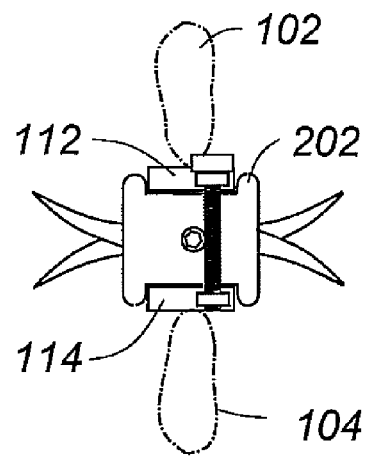
FIG. 4 shows the stabilization apparatus inserted, with the distraction mechanism still in place.

FIG. 3 shows the vertebral bodies being distracted through the operation of distraction system 110, moving the spinous processes 102, 104 apart from one another. This is carried out to an extent that allows the spacer system to be inserted, with the upper and lower surfaces of the spacer system cooperating with the opposing surfaces of the plates 112, 114, as shown in FIG. 4. Again, although the spacer system is shown and described in cooperation with an inventive distraction system 110, the invention is not limited in this regard, in that the spacer may be used in conjunction with any appropriate distraction system, so long as the spacer is inventively accommodated.

Figure 5:
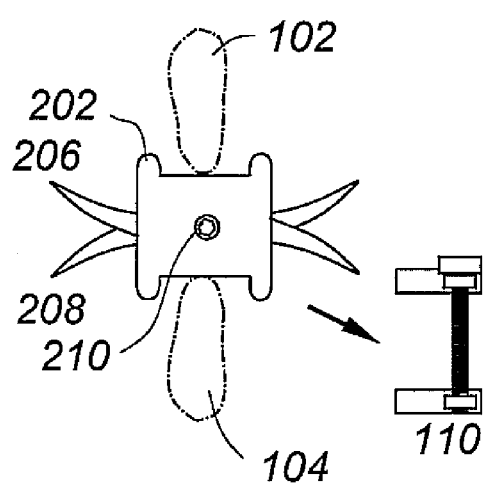
FIG. 5 is a drawing which shows the distraction apparatus being removed.
Figure 6:
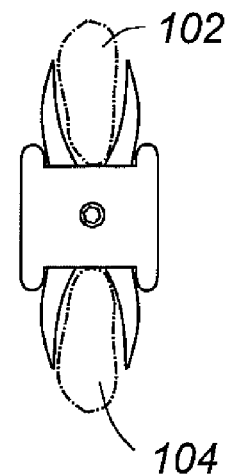
FIG. 6 is a posterior view showing the way in which scissoring elements are locked into place along upper and lower spinous processes to achieve stabilization according to the invention.

In FIG. 5, the distraction system 110 has been removed, allowing spinous processes 102, 104, to rest against the superior and inferior surfaces of the spacer as shown. Next, as shown in FIG. 6, the scissoring elements 206, 208, are rotated upwardly, as shown, thereby stabilizing the superior and inferior spinous processes 102, 104. At this time, the fastener 210 is tightened, locking the mechanism in place, providing a posterior column stabilization system that does not require pedicle implantation.

I claim:

1. A spinal stabilization device, comprising:
    a plate member configured to be placed between an upper spinous process and a lower spinous process, the plate member having an upper surface configured to abut a lower surface of the upper spinous process and a lower surface configured to abut an upper surface of the lower spinous process;
    a pair of scissoring elements coupled to the plate member, each scissoring element being rotatable relative to the plate member, each scissoring element including an upper end that rotates to extend beyond the upper surface of the plate member and a lower end that rotates to extend beyond the lower surface of the plate member, such that inner surfaces of the upper ends of the scissoring elements rotate into contact with opposing outer lateral surfaces of the upper spinous process and inner surfaces of the lower ends of the scissoring elements rotate into contact with opposing outer lateral surfaces of the lower spinous process, wherein the upper ends of the scissoring elements are configured to avoid extending into the upper spinous process and the lower ends of the scissoring elements are configured to avoid extending into the lower spinous process; and
    a locking device configured to secure the scissoring elements in a fixed position, the locking device configured to lock the spinal stabilization device between the upper and lower spinous processes upon rotation of the scissoring elements into contact with the outer lateral surfaces of the upper spinous process and the lower spinous process such that the upper spinous process and the lower spinous process are stabilized by the spinal stabilization device.

2. The spinal stabilization device of claim 1, wherein the inner surfaces of the upper ends and lower ends of the scissoring elements are concave.

3. The spinal stabilization device of claim 1, wherein the locking device is a fastener that extends through the plate member and a central portion of both scissoring elements.

4. The spinal stabilization device of claim 1, wherein the plate member comprises a first plate member, and wherein the stabilization device further comprises:
    a second plate member positioned substantially parallel to the first plate member and configured to be placed between the upper spinous process and the lower spinous process, the second plate member having an upper surface configured to abut a lower surface of the upper spinous process and a lower surface configured to abut an upper surface of the lower spinous process; and
    wherein the scissoring elements are rotatable relative to and positioned between the first plate members and the second plate member.

5. The spinal stabilization device of claim 1, further including:
    a retractor for spreading the upper and lower spinous processes apart to a position in which to receive the plate member.

6. The spinal stabilization device of claim 1, further including:
    a retractor with upper and lower plates for spreading the upper and lower spinous processes apart to receive the plate member; and
    wherein the upper and lower surfaces of the plate member have notches to accommodate the upper and lower plates of the retractor.

7. The spinal stabilization device of claim 1, wherein the plate member further comprises first and second lateral surfaces each extending between the upper surface and lower surface,
    wherein the spinal stabilization device is configured such that, prior to rotation of the scissoring elements, the upper end of each scissoring element extends laterally beyond the first lateral surface and the lower end of each scissoring element extends laterally beyond the second lateral surface.

8. The spinal stabilization device of claim 1, wherein the inner surfaces of the upper ends of the scissoring elements are configured to substantially conform to the outer lateral surfaces of the upper spinous process and the inner surfaces of the lower ends of the scissoring elements are configured to substantially conform to the outer lateral surfaces of the lower spinous process.

9. The spinal stabilization device of claim 1, wherein the upper ends of the scissoring elements are configured to contact the outer lateral surfaces of the upper spinous process in a substantially contiguous manner and the lower ends of the scissoring elements are configured to contact the outer lateral surfaces of the lower spinous process in a substantially contiguous manner.

10. A spinal stabilization device, comprising:
    a plate member configured to be positioned between an upper spinous process and a lower spinous process, the plate member having a superior surface configured to abut a lower surface of the upper spinous process and an inferior surface configured to abut an upper surface of the lower spinous process;
    a pair of scissoring elements coupled to the plate member, each scissoring element being rotatable relative to the plate member, each scissoring element including an upper end and a lower end, the upper end configured to rotate from an insertion configuration in which the upper end extends beyond a first outermost lateral surface of the plate member to a stabilization configuration in which the upper end extends beyond the upper surface of the plate member to contact a lateral surface of a first spinous process, the lower end configured to rotate from the insertion configuration in which the lower end extends beyond a second outermost lateral surface of the plate member to a stabilization configuration in which the lower end extends beyond the lower surface of the plate member, and wherein, when in the stabilization configuration, the upper ends of the scissoring elements contact opposing outer lateral surfaces of the upper spinous process and the lower ends of the scissoring elements contact with opposing outer lateral surfaces of the lower spinous process such that the upper spinous process and the lower spinous process are stabilized by the spinal stabilization device; and
    a locking device configured to secure the scissoring elements in the stabilization configuration.

11. The spinal stabilization device of claim 10, wherein the inner surfaces of the upper ends and the lower ends of the scissoring elements are configured to contact the outer lateral surfaces of the spinous processes in a substantially contiguous manner along a length of the outer lateral surfaces.

12. The spinal stabilization device of claim 10, wherein the inner surfaces of the upper ends of the scissoring elements are configured to substantially conform to the outer lateral surfaces of the upper spinous process and the inner surfaces of the lower ends of the scissoring elements are configured to substantially conform to the outer lateral surfaces of the lower spinous process.

13. The spinal stabilization device of claim 10, wherein the plate member comprises a first plate member, and wherein the interspinous process spacer further comprises:
   a second plate member positioned substantially parallel to the first plate member and configured to be positioned between the upper spinous process and the lower spinous process, the second plate member having a superior surface configured to abut a lower surface of the upper spinous process and an inferior surface configured to abut an upper surface of the lower spinous process; and
   wherein the scissoring elements are disposed between and rotatable relative to the first and second plate members.

14. The spinal stabilization device of claim 10, wherein the locking device comprises a fastener that extends through the plate member and a central portion of both scissoring elements.

15. The spinal stabilization device of claim 10, further comprising:
   a retractor with upper and lower plates for spreading the upper and lower spinous processes apart to receive the plate member with scissoring elements; and
   wherein the superior and inferior surfaces of the plate member have notches to accommodate the upper and lower plates of the retractor.

16. A spinal stabilization device, comprising:
   a plate member configured to be placed between an upper spinous process and a lower spinous process, the plate member having an upper surface configured to abut a lower surface of the upper spinous process and a lower surface configured to abut an upper surface of the lower spinous process;
   a pair of scissoring elements coupled to the plate member, each scissoring element being rotatable relative to the plate member, each scissoring element including an upper end that rotates to extend beyond the upper surface of the plate member and a lower end that rotates to extend beyond the lower surface of the plate member, such that inner surfaces of the upper ends of the scissoring elements rotate into substantially contiguous contact with opposing outer lateral surfaces of the upper spinous process and inner surfaces of the lower ends of the scissoring elements rotate into substantially contiguous contact with opposing outer lateral surfaces of the lower spinous process; and
   a locking device configured to secure the scissoring elements in a fixed position, the locking device configured to lock the spinal stabilization device between the upper and lower spinous processes upon rotation of the scissoring elements into contact with the outer lateral surfaces of the upper spinous process and the lower spinous process such that the upper spinous process and the lower spinous process are stabilized by the spinal stabilization device.

17. The spinal stabilization device of claim 16, wherein the inner surfaces of the upper ends and lower ends of the scissoring elements are concave.

18. The spinal stabilization device of claim 16, wherein the plate member comprises a first plate member, and wherein the stabilization device further comprises:
   a second plate member positioned substantially parallel to the first plate member and configured to be placed between the upper spinous process and the lower spinous process, the second plate member having an upper surface configured to abut a lower surface of the upper spinous process and a lower surface configured to abut an upper surface of the lower spinous process; and
   wherein the scissoring elements are rotatable relative to and positioned between the first plate members and the second plate member.

19. The spinal stabilization device of claim 16, wherein the upper ends of the scissoring elements are configured to avoid extending into the upper spinous process and the lower ends of the scissoring elements are configured to avoid extending into the lower spinous process.

20. The spinal stabilization device of claim 16, wherein the inner surfaces of the upper ends of the scissoring elements are configured to substantially conform to the outer lateral surfaces of the upper spinous process and the inner surfaces of the lower ends of the scissoring elements are configured to substantially conform to the outer lateral surfaces of the lower spinous process.

* * * * *